(12) United States Patent
Hong et al.

(10) Patent No.: US 8,100,527 B2
(45) Date of Patent: Jan. 24, 2012

(54) INTERMEDIATE VISION WITH PHAKIC MULTIFOCAL OPTICS UTILIZING RESIDUAL ACCOMMODATIONS

(75) Inventors: Xin Hong, Arlington, TX (US); Mutlu Karakelle, Fort Worth, TX (US); Xiaoxiao Zhang, Fort Worth, TX (US)

(73) Assignee: Novartis AG, Basel (CH)

( * ) Notice: Subject to any disclaimer, the term of this patent is extended or adjusted under 35 U.S.C. 154(b) by 333 days.

(21) Appl. No.: 12/522,949

(22) PCT Filed: Jan. 11, 2008

(86) PCT No.: PCT/US2008/050860
§ 371 (c)(1),
(2), (4) Date: Jul. 13, 2009

(87) PCT Pub. No.: WO2008/089063
PCT Pub. Date: Jul. 24, 2008

(65) Prior Publication Data
US 2010/0016962 A1    Jan. 21, 2010

Related U.S. Application Data

(60) Provisional application No. 60/884,688, filed on Jan. 12, 2007.

(51) Int. Cl.
G02C 7/02     (2006.01)
A61F 2/16     (2006.01)
(52) U.S. Cl. ......... 351/159; 351/161; 623/6.3; 623/6.36
(58) Field of Classification Search .................. None
See application file for complete search history.

(56) References Cited

U.S. PATENT DOCUMENTS

| 6,562,070 | B2 | 5/2003 | Tran et al. |
| 7,481,532 | B2 | 1/2009 | Hong et al. |
| 2004/0230299 | A1 | 11/2004 | Simpson |
| 2006/0098163 | A1 | 5/2006 | Bandhauer |
| 2006/0116764 | A1 | 6/2006 | Simpson |
| 2007/0182917 | A1 | 8/2007 | Zhang |
| 2007/0182921 | A1 | 8/2007 | Zhang |

FOREIGN PATENT DOCUMENTS

| WO | 2006090477 A1 | 5/2006 |
| WO | 2006060480 A1 | 6/2006 |
| WO | WO 2006/060477 | 6/2006 |

OTHER PUBLICATIONS

International Preliminary Examination Report; PCT/US2008/050860; Jul. 23, 2009.

*Primary Examiner* — David H Willse
*Assistant Examiner* — Javier Blanco
(74) *Attorney, Agent, or Firm* — Jonathan E. Prejean

(57) ABSTRACT

In one aspect, the present invention provides a method of correcting vision, which comprises determining a residual accommodation exhibited by a natural, crystalline lens of an eye, and selecting a multifocal intraocular lens (IOL), which exhibits a far-focus optical power (e.g., in a range of about −15 to about +50 Diopters (D)) and an add power (e.g., in a range of about 1 D to about 4 D), for implantation in the eye while retaining the natural lens. The add power of the IOL is selected as a function of the residual accommodation such that a combination of the IOL and the natural lens provides a visual contrast greater than about 10% at a spatial frequency of about 20 cycles/degree for viewing objects at a distance greater than about 30 cm from the eye.

5 Claims, 8 Drawing Sheets

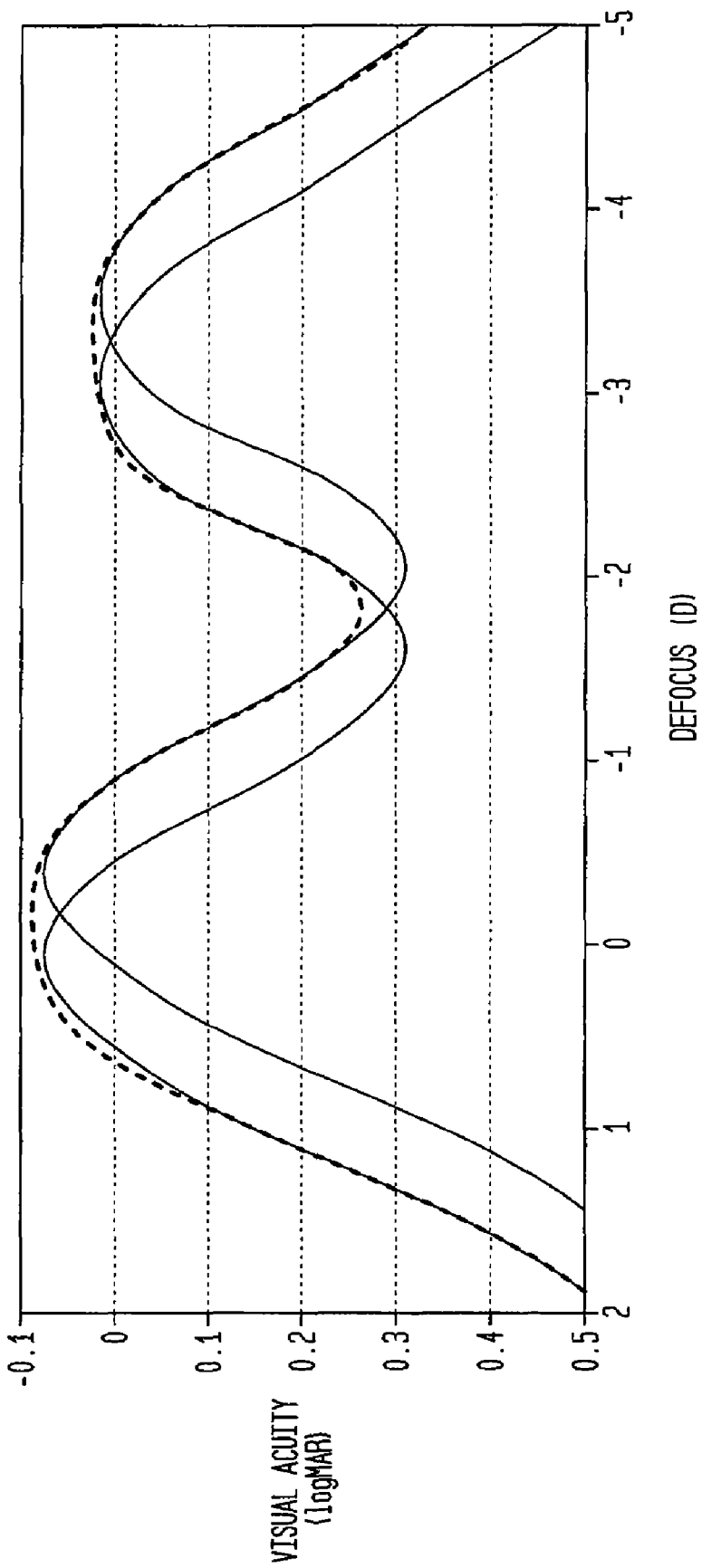

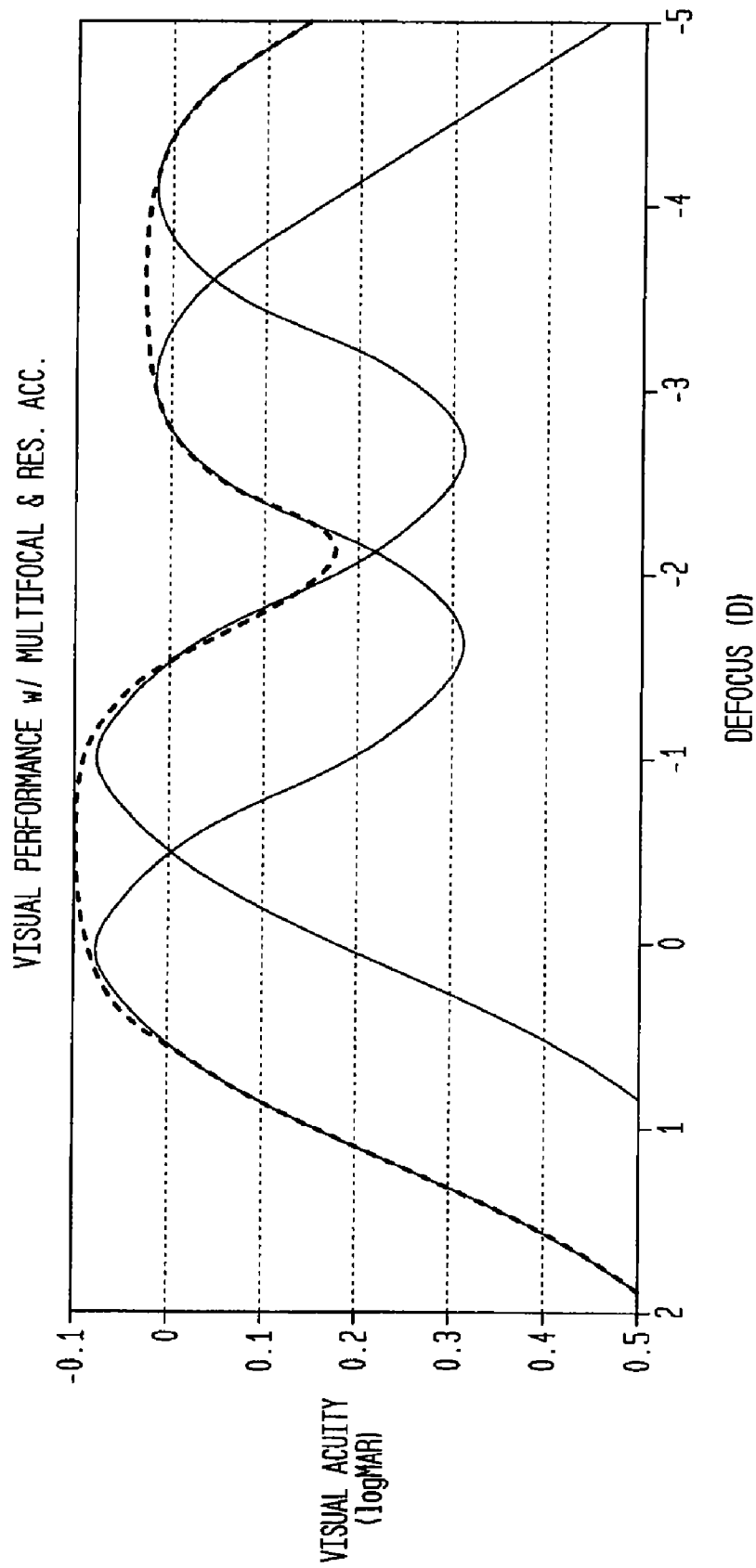

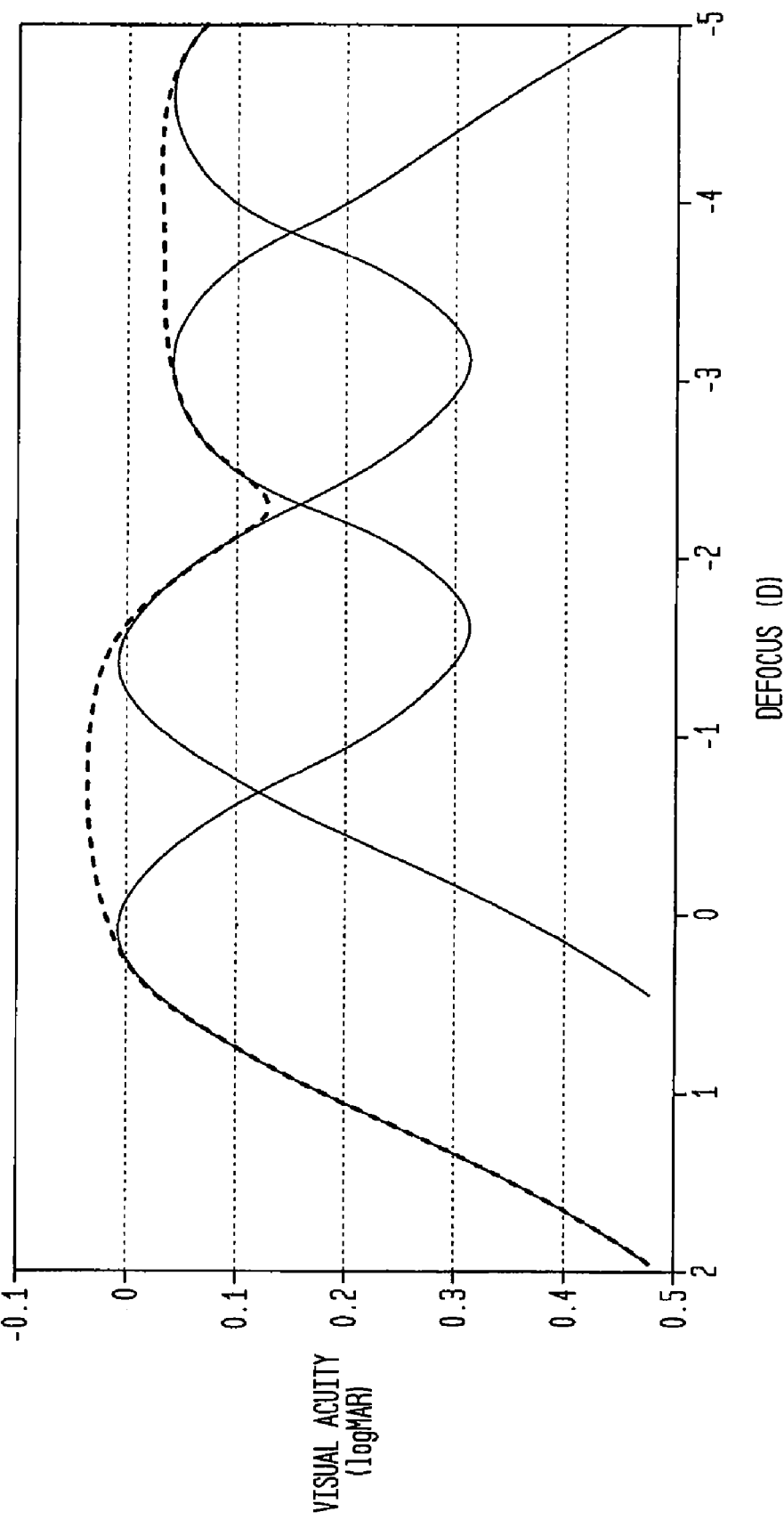

PREDICTED FOR 2.0D RESIDUAL ACCOMMODATION

INTERMEDIATE VISION WITH PHAKIC MULTIFOCAL OPTICS UTILIZING RESIDUAL ACCOMMODATIONS

This application claims priority as a 371 application from PCT/US2008/050860 filed on Jan. 11, 2008, and claims priority from U.S. Patent Application Ser. No. 60/884,688, filed on Jan. 12, 2007.

BACKGROUND

The present invention relates generally to methods for correcting vision, and more particularly to such methods for enhancing vision in phakic eyes by utilizing intraocular lenses (IOLs).

The optical power of the eye is determined by the optical power of the cornea and that of the crystalline lens, with the lens providing about a third of the eye's total optical power. The lens is a transparent, biconvex structure whose curvature can be changed by ciliary muscles for adjusting its optical power so as to allow the eye to focus on objects at varying distances. This process is known as accommodation. As the individual ages, the crystalline lens enlarges and hardens, rendering the adjustment of its optical power by the ciliary muscles increasingly difficult. This degradation of the accommodative ability of the eye is known as presbyopia whose earliest symptom is difficulty in seeing close objects.

Hence, there is a need for methods of correcting and enhancing vision of individuals who suffer from presbyopia.

SUMMARY

In one aspect, the present invention provides a method of correcting vision, which comprises determining a residual accommodation exhibited by a natural, crystalline lens of an eye, and selecting a multifocal intraocular lens (IOL), which exhibits a far-focus optical power (e.g., in a range of about −15 to about +50 Diopters (D)) and an add power (e.g., in a range of about 1 D to about 4 D), for implantation in the eye while retaining the eye's natural lens. The add power of the IOL is selected as a function of the residual accommodation such that a combination of the IOL and the natural lens provides a visual contrast greater than about 10% at a spatial frequency of about 20 cycles/degree for viewing objects at a distance greater than about 30 cm from the eye.

In a related aspect, the visual contrast can be determined by employing a through-focus modulation transfer function, e.g., at a selected radiation wavelength (e.g., 550 nm) and for a given aperture size (e.g., 3 mm).

In another aspect, the add power of the IOL is selected at a value in a range of about 1 D to about 2.5 D such that the far-focus power of the IOL provides distance vision, the near-focus power of the IOL provides intermediate vision and a combination of the near-focus power of the IOL and the residual accommodation of the natural crystalline lens provides near vision.

In another aspect, the add power of the IOL is selected at a value in a range of about 2.5 D to about 4.5 D such that the far-focus power of the IOL provides distance vision, the near-focus power of the IOL provides near vision, and a combination of the far-focus power of the IOL and the residual accommodation of the natural crystalline lens provides intermediate vision.

In other aspects, in the above method of correcting vision, the depth-of-focus associated with a near focus of the IOL is selected based on the natural lens's residual accommodation such that a shift of the add power by the residual accommodation would result in near vision with a visual contrast greater than about 10% at a spatial frequency of about 20 cycles/degree.

In a further aspect, in the above method of correcting vision, the depth-of-focus associated with the far focus of the IOL is selected based on the natural lens's residual accommodation such that a shift of the far focus by the natural lens's residual accommodation would result in providing intermediate vision with a visual contrast greater than about 10% at a spatial frequency of about 20 cycles/degree.

In other aspects, the invention provides intraocular lenses suitable for implantation in a phakic eye. By way of example, such a lens can comprise an optic that provides a far focus and a near focus characterized by an add power in a range of about 1 D to about 4.5 D, wherein the depth-of-focus associated with at least one of those foci is greater than about 1 D (e.g., in a range of about 1 D to about 4.5 D). The far-focus optical power can be, e.g., in a range of about −15 D to about +50 D.

In some cases, in the above phakic IOL, the aforementioned depth-of-focus can be in a range of about 1 D to about 2.5 D for an add power in a range of about 1 D to about 2.5 D. In other cases, the depth-of-focus at one or both foci of the IOL can be in a range of about 2.5 D to about 4.5 D for an add power in a range of about 2.5 D to about 4.5 D.

In another aspect, the above phakic IOL comprises an anterior and a posterior optical surface configured to provide the far focus, and a diffractive structure disposed on one of those surfaces to provide the add power. In some cases, the diffractive structure can include a plurality of diffractive zones separated from one another by steps whose heights decrease as a function of increasing distance from an optical axis of the lens. In other cases, the diffractive structure can exhibit uniform step heights.

In another aspect, a method of correcting vision is disclosed that includes determining a residual accommodation exhibited by a natural, crystalline lens of an eye, and selecting a multifocal intraocular lens (IOL) that provides a far-focus and a near-focus optical power for implantation in the eye while retaining the natural lens. The depth-of-focus associated with the far or near focus is selected such that a shift of the far or near focus by the residual accommodation would result in intermediate or near vision, respectively, with a visual contrast greater than about 10% at a spatial frequency of about 20 cycles/degree.

In a related aspect, in the above method, the near-focus optical power is selected such that the far-focus power of the IOL facilitates distance vision, the near-focus power of the IOL provides intermediate vision and a combination of the near-focus power of the IOL and the residual accommodation of the natural crystalline lens provides near vision. By way of example, the near-focus can be characterized by an add power in a range of about 1 D to about 2.5 D.

In another aspect, in the above method, the near-focus optical power is selected such that the far-focus power of the IOL facilitates distance vision, the near-focus power of the IOL provides near vision, and a combination of the far-focus power of the IOL and the residual accommodation of the natural, crystalline lens provides intermediate vision. By way of example, the near-focus power can be characterized by an add power in a range of about 2.5 D to about 4.5 D.

Further understanding of the invention can be obtained by reference to the following detailed description in conjunction with the associated drawings, which are described briefly below.

DETAILED DESCRIPTION

The present invention generally provides methods, as well as ophthalmic lenses for practicing those methods, for enhancing vision provided by a phakic eye whose natural crystalline lens exhibits a degraded accommodation. For example, the invention provides methods for implanting an intraocular lens (IOL) in a phakic eye whose crystalline lens exhibits some residual accommodation (e.g., less than about 2 Diopters) so as to improve the patient's vision by employing the near and far focusing powers of the IOL as well as the residual accommodation of the natural lens. The term "intraocular lens" and its abbreviation "IOL" are used herein interchangeably to describe lenses that are implanted into the interior of an eye to enhance vision. In the embodiments that follow, such IOLs are implanted in an eye that retains its natural crystalline lens (such IOLs are herein also referred to as phakic IOLs).

Figure 1:
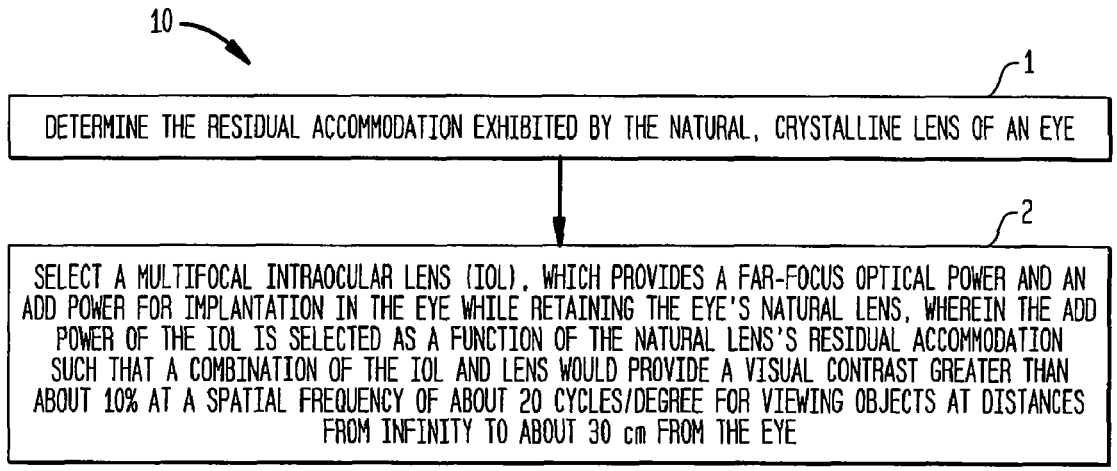
FIG. 1 presents a flow chart depicting various steps in an exemplary method of correcting vision in accordance with one embodiment of the invention, FIG. 2 schematically depicts hypothetical through-focus visual acuity curve corresponding to a combination of an IOL having an add power of about 2 D and the natural lens of a phakic eye in which the IOL is implanted, where the natural lens exhibits a residual accommodation of about 1 D, FIG. 3 schematically depicts hypothetical through-focus visual acuity curve corresponding to a combination of an IOL having an add power of about 4 D and the natural lens of a phakic eye in which the IOL is implanted, where the natural lens exhibits a residual accommodation of about 2 D, FIG. 4 schematically illustrates an exemplary diffractive IOL suitable for use in the practice of the invention, FIG. 5 schematically depicts an IOL implanted in the anterior chamber of a phakic eye in front of the iris in accordance with some embodiments of the invention, FIG. 6A schematically depicts calculated binocular visual acuity curves as a function of defocus for a combination of a hypothetical multifocal IOL and the natural lens of a phakic eye in which the IOL is implanted, where the natural lens is assumed to exhibit a residual accommodation of about 0.5 D, FIG. 6B schematically depicts calculated binocular visual acuity curves as a function of defocus for a combination of a hypothetical multifocal IOL and the natural lens of a phakic eye in which the IOL is implanted, where the natural lens is assumed to exhibit a residual accommodation of about 1 D, FIG. 7A schematically depicts calculated binocular visual acuity curves as a function of defocus for a combination of a hypothetical multifocal IOL and the natural lens of a phakic eye in which the IOL is implanted, where the natural lens is assumed to exhibit a residual accommodation of about 1.5 D, and FIG. 7B schematically depicts calculated binocular visual acuity curves as a function of defocus for a combination of a hypothetical multifocal IOL and the natural lens of a phakic eye in which the IOL is implanted, where the natural lens is assumed to exhibit a residual accommodation of about 2 D.

With reference to a flow chart 10 in FIG. 1, in some exemplary embodiments, a method of correcting vision according to the teachings of the invention includes determining a residual accommodation exhibited by a natural, crystalline lens of an eye (step 1), and selecting a multifocal intraocular lens (IOL), which exhibits a far-focus optical power and an add power for generating a near-focus optical power, for implantation in the eye while retaining the natural lens (step 2). The residual accommodation of the natural lens can be determined by utilizing methods known in the art. The add power of the IOL is selected as a function of the natural lens's residual accommodation such that a combination of the IOL and the lens would provide a visual contrast greater than about 10% at a spatial frequency of about 20 cycles/degree for viewing objects at distances from infinity to about 30 cm, or to about 50 cm, from the eye.

In some cases, the visual contrast can be determined by a through-focus modulation transfer function (MTF) obtained at a given spatial frequency (e.g., at 20 cycles/degree). As known to those having ordinary skill in the art, an MTF of an imaging system, such as the combination of the IOL and the natural lens, can be defined as a ratio of contrast associated with an image of an object formed by the system relative to a contrast associated with the object. The MTF associated with an optical system depends generally not only on the spatial frequency of the intensity distribution of the light illuminating the imaging system, but it can also be affected by other factors, such as the size of an illumination aperture as well as the wavelength of the illuminating light. In many embodiments, the MTF can be measured and/or calculated for light having a wavelength of about 550 nm—though other wavelengths or a combination of wavelengths can also be employed—at an aperture size of about 3 mm. By way of example, the through-focus MTF, indicative of the visual contrast provided by a combination of the IOL and the natural lens, can be obtained by utilizing a model eye incorporating the IOL and the natural lens, e.g., via raytracing. Alternatively, or in addition, the visual contrast can be determined, by employing Snellen eye charts.

In many embodiments, the far-focusing optical power of the phakic IOL lies in a range of about −15 D to about +50 D, and can be selected so as to augment and/or correct the focusing power of the natural lens when in a relaxed state. The add power of the IOL can be, e.g., in a range of about 1 D to about 4.5 D. The add power can be selected based on the residual accommodation of the natural lens as well as the visual needs of a patient so as to leverage the natural lens's accommodative ability for providing enhanced intermediate or near vision, as discussed further below.

By way of example, the add power of the phakic IOL can be selected to be in a range of about 1 D to about 2.5 D such that the far-focus power of the IOL provides distance vision (in combination of the optical power of the cornea and that of the natural lens when in a relaxed state), the near-focus power of the IOL provides intermediate vision and a combination of the near-focus power of the IOL and the residual accommodation of the natural crystalline lens provides near vision.

The term "distance vision" generally refers to the ability to view objects at distances greater than about 80 cm. More specifically, in the context of the present application, a phakic IOL, either by itself or in combination with the accommodative power of the natural lens, provides distance vision if the visual contrast associated with an image of an object located at a distance greater than about 80 cm from the eye is greater than about 10% at a spatial frequency of about 20 cycles/degree. The term "near vision" generally refers to the ability to view objects at distances less than about 45 cm, e.g., in a range of about 30 cm to about 45 cm. More specifically, in the context of the present application, a phakic IOL, either by itself or in combination with the accommodative power of the natural lens, is considered to provide near vision if the visual contrast associated with an image of an object located in a range of about 30 cm to about 45 cm from the eye is greater than about 10% at a spatial frequency of about 20 cycles/degree.

Further, the term "intermediate vision" generally refers to the ability to view objects at distances in a range of about 45 cm to about 80 cm from the eye. More specifically, in the context of the present application, a phakic IOL, either by itself or in combination with the accommodative power of the natural lens, is considered to provide intermediate vision if the visual contrast associated with an image of an object located in a range of about 45 cm to about 80 cm from the eye is greater than about 10% at a spatial frequency of about 20 cycles/degree. In order to assess the capability of the IOL by itself, or in combination with the natural lens, to provide distance, intermediate and near vision, the visual contrast can be determined, e.g., by measuring or calculating the modulation transfer function (MTF) in a model eye comprising models of the phakic IOL, the natural lens, and an average human cornea (e.g., a cornea with an asphericity characterized by a conic constant of about 0.18). Alternatively, the visual contrast can be determined by measuring the visual acuity of a patient's eye having the phakic IOL.

Figure 2:
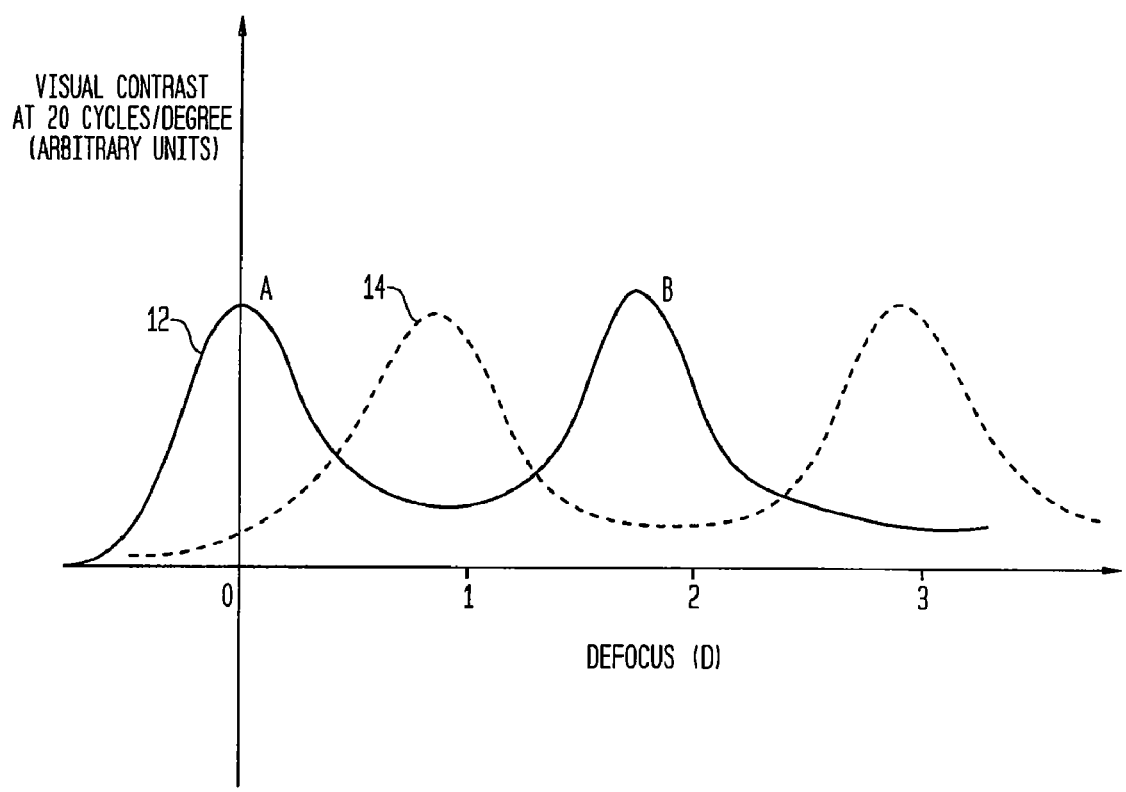

As noted above, in some embodiments in which the add power of the IOL lies in a range of about 1 D to about 2.5 D, the combination of the near focus power of the IOL and the residual accommodation of the natural lens provides the patient with near vision. By way of further illustration, FIG. 2 schematically depicts a hypothetical through-focus visual acuity curve 12 of a combination of an IOL and the natural lens of a phakic eye in which the IOL is implanted. The curve 12 depicts a far-focus optical power (A) (e.g., in a range of about −15 to about +34 Diopters) provided by the combined IOL and the natural lens (depicted here arbitrarily as corresponding to zero defocus), and an add power (B) of about 2 D provided by the IOL, when the natural lens is in a relaxed state (i.e., in the absence of accommodation). The far-focusing power provides vision for viewing objects at far distances (e.g., distances greater than about 80 cm from the eye) and the add power provides vision at intermediate distances (e.g., viewing distances in a range of about 45 cm to about 80 cm from the eye), without any accommodation from the natural lens.

The accommodation of the natural lens can, however, be utilized to shift the curve A such that a combination of the near-focus and the residual accommodation would provide vision at near distances. By way of example, curve 14 (shown in dashed lines) corresponds to a through-focus visual acuity provided by the IOL in combination with the maximum accommodation (e.g., about 1 D) of the eye's natural lens. This curve shows that the near-focusing power of the IOL has been shifted via the natural lens's residual accommodation so as to provide near vision (the peak of the near-focus power has been shifted to a defocus value of about 3 D). In addition, the far-focusing power of the IOL has also been shifted to enhance vision in the far-intermediate region, i.e., the region between the static (i.e., in absence of accommodation) peaks of the near and far foci. Hence, as the accommodation of natural lens increases from zero to its maximum value, the through-focus visual contrast curve shifts from curve A to B, thus providing vision from far to near distances.

Figure 3:
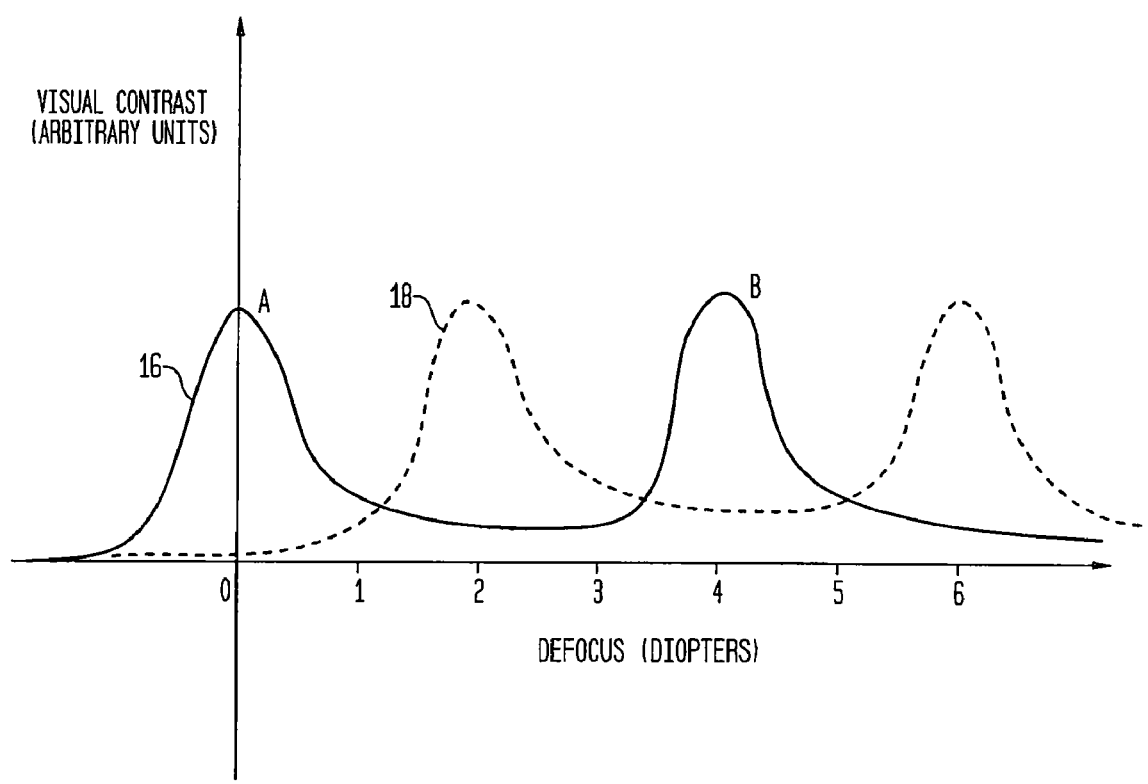

In some other embodiments, the add power of the IOL can be selected to be in a range of about 2.5 D to about 4.5 D such that the far-focus power of the IOL facilitates distance vision, the near-focus power of the IOL provides near vision, and a combination of the far-focus power of the IOL and the residual accommodation of the natural lens provides intermediate vision. By way of further illustration of such embodiments, FIG. 3 schematically depicts the focusing characteristics of a combination of a hypothetical phakic IOL, which exhibits an add power of about 4 D, and the natural lens of an eye in which the IOL is implanted in the form of visual contrast as a function of defocus, where the zero defocus is selected to correspond to the far focus provided by the IOL and the natural lens. The natural lens is assumed to provide a residual accommodation of about 2 D. A curve 16 schematically depicts the visual contrast of the combined IOL and the natural lens as a function of defocus. In absence of any accommodation by the natural lens (i.e., when the natural lens is in its relaxed state), the far focus (designated as A) facilitates far vision, that is, the ability to focus on objects located at distances greater than about 80 cm from the eye, while the near focus of the IOL (designated as B) provides near vision, that is, the ability to focus on objects located at distances less than about 45 cm, e.g., in a range of about 30 cm to about 45 cm, from the eye.

The residual accommodation of the natural lens, however, allows shifting the focusing power of the IOL so as to provide intermediate vision. A curve 18 (shown in dashed lines) schematically depicts such a shift in the focusing power of the IOL for a maximum accommodation of the natural lens. In other words, as the natural lens is compressed to provide increasing accommodation, the through-focus acuity curve shifts from the curve 16 to the curve 18. Through this shift, additional visual contrast is provided for viewing objects at intermediate distances, that is, intermediate vision is enhanced. Of course, the accommodation by the natural lens also moves the peak associated with the near-focus of the IOL to larger defocus values (corresponding to smaller viewing distances). However, in this embodiment, the IOL is selected to have a relatively large add power (e.g., about 4 D) that provides a static near focusing power (that is, near focusing power when the natural lens is in a relaxed state) that is sufficiently strong for viewing near objects (e.g., objects located at distances in a range of about 30 cm to about 45 cm from the eye). Hence, in this embodiment, the residual accommodation, though helpful, is not essential for near vision.

In many embodiments, the depth-of-focus at one or more foci of the multifocal phakic IOL is selected based on the natural lens's residual accommodation and its add power so as to optimize visual accommodative enhancement of the eye. The terms "depth-of-field" and "depth-of-focus," which are used interchangeably here, are well known in the context of a lens (or a lens system) and are readily understood by those having ordinary skill in the art as referring to the distances in the object and image spaces over which an acceptable image can be resolved. To the extent that a more quantitative measure might be needed, the terms "depth-of-focus" and "depth-of-field" can refer to an amount of defocus associated with an optical system (e.g., a lens or the lens or a combination of lenses) at which a through-focus modulation transfer function (MTF) of the optical system, measured (or calculated) with a 3 mm aperture and green light, e.g., light having a wavelength of about 550 nm, exhibits a contrast of at least about 10% at a spatial frequency of about 20 cycles/degree. Other definitions can also be applied and it should be clear that depth-of-focus is influenced by many factors including, for example, aperture size, chromatic content of light, and base power of the lens itself. Nonetheless, the MTF test, described above and discussed further below, is presented as a straightforward test for determining the depth-of-focus. In the case of a multifocal lens, the above definition can be applied with regard to the depth-of-focus at each of the multiple foci of the lens.

By way of example, in some embodiments in which the IOL's add power lies in a range of about 1 to about 2.5 D, the depth-of-focus associated with the IOL's near focus can be selected based on the residual accommodation of the eye's natural lens such that a shift of the add power by the residual accommodation would result in a near vision with a visual contrast greater than about 10% at a spatial frequency of about 20 cycles/degree. For example, in such embodiments, the depth-of-focus associated with the near focus of the IOL can be in a range of about 1 D to about 2.5 D. Generally, in many cases, as the residual accommodation decreases, the selected depth-of-focus increases.

In other embodiments in which the IOL's add power lies in a range of about 2.5 D to about 4.5 D, the depth-of-focus associated with the IOL's far focus can be selected based on the residual accommodation of the natural lens such that a shift of the far focus by the residual accommodation would result in intermediate vision with a visual contrast greater than about 10% at a spatial frequency of about 20 cycles/degree. For example, in such embodiments, the depth-of-focus associated with the far focus of the IOL can be in a range of about 2.5 D to about 4.5 D. Again, in many cases, the IOL is selected to exhibit a higher depth-of-focus for a lower residual accommodation.

Figure 4:
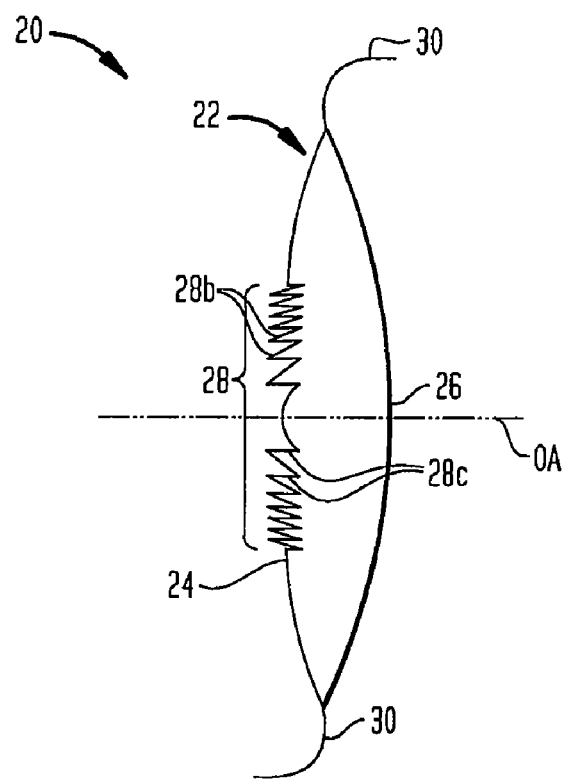

A variety of IOLs can be utilized in the practice of the invention. By way of example, FIG. 4 schematically shows such a multifocal IOL 20 having an optic 22, which is preferably formed of a soft foldable biocompatible material. Some examples of such materials include, without limitation, hydrogel, silicone and soft acrylic polymers (e.g., a material used to form commercially available lenses sold under the trademark Acrysof®). The optic 22, which comprises an anterior surface 24 and a posterior surface 26, provides a far-focus power, e.g., in a range of about −15 D to about +50 D (and preferably in a range of about −5 D to about 34 D). In some embodiments, a diffractive structure 28 disposed on the anterior surface 24 provides the IOL with an add power in a range of about 1 D to about 2.5 D, while in other embodiments the diffractive structure 28 is configured to provide an add power in a range of about 2.5 D to about 4.5 D.

The lens 20 further includes a plurality of fixation members or haptics 30, which are also formed of well known suitable biocompatible materials, that facilitate placement of lens 20 in the eye. The fixation members are preferably designed in a manner known in the art to ensure that the IOL can remain in the eye without causing any adverse effects over a long period, e.g., ten years or more. Some examples of plate-style haptics suitable for use in phakic IOLs are described in U.S. Pat. No. 6,562,070 entitled "Anterior Chamber Phakic Lens," which is herein incorporated by reference.

In some embodiments, the diffractive structure is characterized by a plurality of diffractive zones separated from one another by a plurality of steps that exhibit a decreasing height as a function of increasing distance from the optical axis. In other words, the step heights at the boundaries of the diffractive zones are "apodized" so as to modify the fraction of optical energy diffracted into the near and far foci as a function of aperture size (e.g., as the aperture size increases, more of the light energy is diffracted to the far focus). By way of example, the step height at each zone boundary can be defined in accordance with the following relation:

$$\text{Step height} = \frac{\lambda}{a(n_2 - n_1)} f_{apodize} \qquad \text{Equation (1)}$$

wherein
$\lambda$ denotes a design wavelength (e.g., 550 nm),
a denotes a parameter that can be adjusted to control diffraction efficiency associated with various orders, e.g., a can be selected to be 2.5;
$n_2$ denotes the index of refraction of the optic,
$n_1$ denotes the refractive index of a medium in which the lens is placed, and $f_{apodize}$ represents a scaling function whose value decreases as a function of increasing radial distance from the intersection of the optical axis with the anterior surface of the lens. By way of example, the scaling function $f_{apodize}$ can be defined by the following relation:

$$f_{apodize} = 1 - \left(\frac{r_i}{r_{out}}\right)^3. \qquad \text{Equation (2)}$$

wherein
$r_i$ denotes the radial distance of the $i^{th}$ zone,
$r_{out}$ denotes the outer radius of the last bifocal diffractive zone. Other apodization scaling functions can also be employed, such as those disclosed in a co-pending patent application entitled "Apodized Aspheric Diffractive Lenses," filed Dec. 1, 2004 and having a Ser. No. 11/000,770, which is herein incorporated by reference.

In some embodiments, the diffractive zones are in the form of annular regions that extend about the optic's optical axis. In some of such embodiments, the radial location of a zone boundary ($r_i$) is selected in accordance with the following relation:

$$r_i^2 = (2i+1)\lambda f \qquad \text{Equation (3)}$$

wherein
i denotes the zone number (i=0 denotes the central zone),
$r_i$ denotes the radial location of the ith zone,
$\lambda$ denotes the design wavelength, and
$f$ denotes an add power.

In some embodiments, the depth-of-focus at the near and/or far focus can be adjusted by selectively varying the areas of the annular diffraction zones. By way of example, the radial location of a zone boundary can be determined in accordance with the following relation:

$$r_i^2 = (2i+1)\lambda f + g(i) \qquad \text{Equation (4).}$$

wherein
i denotes the zone number (i=0 denotes the central zone),
$\lambda$ denotes the design wavelength,
$f$ denotes a focal length of the near focus, and
g(i) denotes a non-constant function.

In some cases, the function g(i) is defined in accordance with the following relation:

$$g(i) = (ai^2 + bi)f \qquad \text{Equation (5),}$$

wherein
i denotes the zone number,
a and b are two adjustable parameters, and
$f$ denotes the focal length of the near focus. By way of example, a can be in a range of about $0.1\lambda$ to about $0.3\lambda$, and b can be in a range of about $1.5\lambda$ to about $2.5\lambda$, where $\lambda$ denotes the design wavelength. By adjusting the function g(i), the depth-of-focus associated with the near and/or far focus can be varied. For example, the through-focus visual contrast curve associated with those foci can be broadened, which can result in diverting some of the incident light to intermediate focal region.

In some embodiments, the depth-of-focus at the foci of the diffractive lens be adjusted by selecting the profiles of the steps separating the diffractive zones. For example, while in some embodiments, the steps have sawtooth-like profiles, in other embodiments, they can be in the form of straight edges.

In some embodiments, a trifocal IOL can be implanted in a phakic eye so as to provide, together with the residual accommodation of the eye's natural lens, enhanced vision extending from near to far vision. By way of example, a trifocal lens having a far focus power (e.g., in a range of about −15 D to about +50 D), a near-focus add power (e.g., in a range of about 3 D to about 9 D) and an intermediate-focus add power (e.g., in a range of about 1.5 D to about 4.5 D) can be implanted in the eye while retaining the eye's natural lens. The residual accommodation of the natural lens can shift a through-focus visual contrast curve associated with the trifocal IOL to fill in the notches of visual contrast deficit between the static (in absence of accommodation) visual contrast peaks associated with the far, intermediate and near foci of the IOL so as to provide a desired visual contrast (e.g., a contrast greater than about 10% at a spatial frequency of about 20 cycles/degree) extending from near to far vision. Some examples of trifocal IOLs suitable for use in the practice of the invention are disclosed in pending U.S. patent application entitled "Pseudo-Accommodative IOL Having Diffractive Zones With Varying Areas" having a Ser. No. 11/350,437, filed on Feb. 9, 2006; and in U.S. patent application entitled "Pseudo-Accommodative IOL Having Multiple Diffractive Patterns" having a Ser. No. 11/350,497, and filed on Feb. 9, 2006. Both of these applications are herein incorporated by reference.

Figure 5:
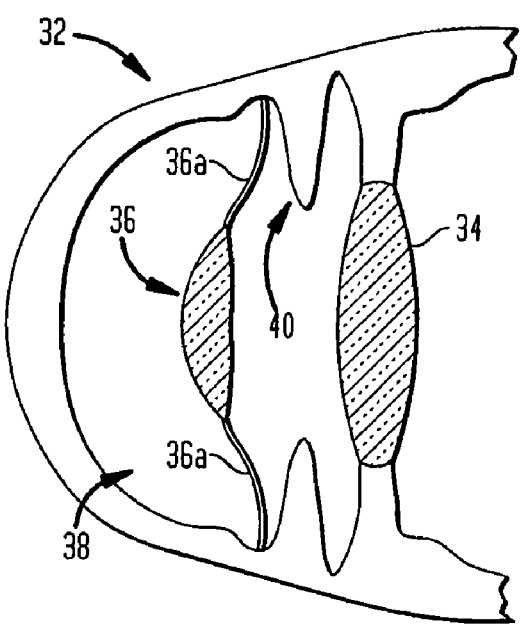

In some embodiments of the invention, the phakic IOL can be implanted in the anterior chamber of the eye. For example, FIG. 5 schematically depicts an eye 32 having a natural crystalline lens 34 in which an IOL 36 accordingly to the teachings of the invention is implanted. More specifically, the IOL is implanted in the anterior chamber 38 of the eye in front of the iris 40 with its fixation members 36a facilitating the retention of lens in its proper position and orientation. Alternatively, the lens 36 can be implanted in the anterior chamber behind the iris. Of course, any other suitable implantation method can also be employed.

To further illustrate some salient features of the invention, the following hypothetical examples are provided. It should be understood that these examples are provided only for illustrative purposes and are not intended to necessarily indicate optimal results that can be obtained by practicing the vision correction methods of the invention.

Example 1

FIG. 6A schematically depicts calculated binocular visual acuity curves as a function of defocus for a combination of a hypothetical multifocal IOL implanted in a phakic eye having a natural, crystalline lens that exhibits a residual accommodation of about 0.5 D. The curve A, which indicates the static (i.e., in absence of accommodation) focusing characteristics of the IOL, shows that the IOL is characterized by a far-focusing power (shown as zero defocus) and an add power of 3 D. The static curve A can be shifted via accommodative effects of the natural lens to obtain the visual acuity curve B at a maximum accommodation (here 0.5 D). This shift enhances the visual acuity for intermediate vision. The curve C depicted in dashed lines shows a resultant dynamic through-focus curve enveloping visual acuity curves corresponding to different accommodations (from 0 to about 0.5 D).

Example 2

With reference to FIG. 6B, this example employs the same multifocal IOL as that in the previous example, but assumes a larger residual accommodation of the natural lens (an accommodation of about 1 D). Similar to the previous example, the curve A depicts the static through-focus visual acuity provided by the IOL, and the curve B depicts the through-focus visual acuity provided by a combination of the IOL and the maximum accommodation of the natural lens. Further, the curve C (shown in dashed lines) is a resultant dynamic through-focus visual acuity curve enveloping the visual acuity curves corresponding to different accommodations, showing enhanced vision especially at intermediate distances.

Example 3

With reference to FIG. 7A, this example utilizes the same multifocal IOL as in the previous examples, but assumes that the natural, crystalline lens provides a residual accommodation of 1.5 D. Again, the curves A and B show, respectively, the static through-focus visual acuity as well as the through-focus visual acuity at maximum accommodation. The resultant curve C shows an envelope of visual acuity curves at different accommodations, indicating that the larger residual accommodation has resulted in further filling of notches of visual acuity deficit for intermediate vision.

Example 4

Figure 7B:
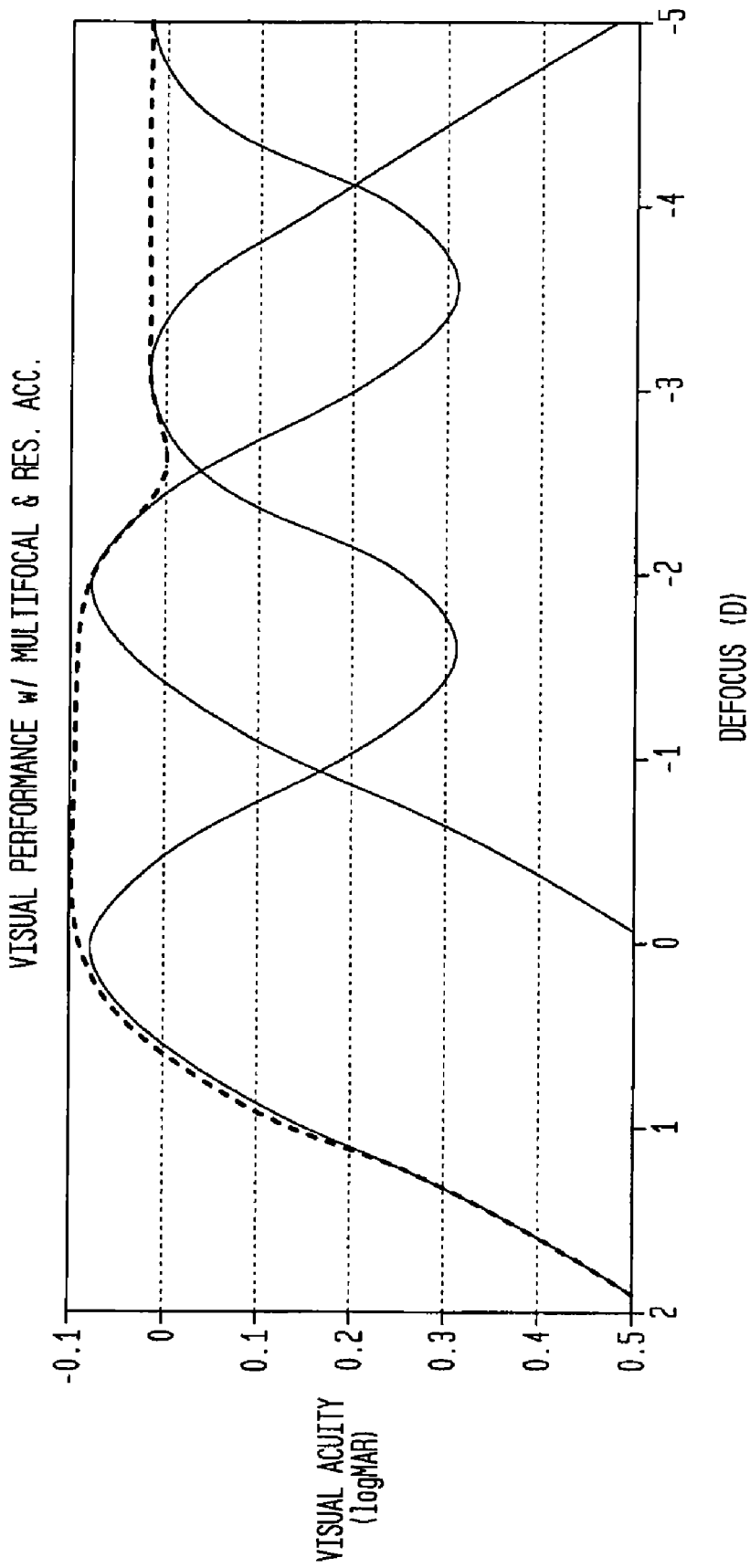

With reference to FIG. 7B, this example employs the same multifocal IOL as in the previous examples, but assumes that the natural, crystalline lens provides a residual accommodation of 2 D. Again, the curves A and B show, respectively, the static through-focus visual acuity and the through-focus visual acuity at maximum accommodation. The resultant curve C shows an envelope of visual acuity curves at different accommodations, indicating that at this residual accommodation, the combination of IOL and the lens provides an enhanced visual acuity in a range of distances extending from near to far vision.

Those having ordinary skill in the art will appreciate that various changes can be made to above embodiments without departing from the scope of the invention.

What is claimed is:

1. A multifocal, phakic intraocular lens (IOL) suitable for implantation in an eye while retaining the natural crystalline lens, comprising:
   an optic providing a far focus and a near focus characterized by an optical power and an add power, the add power being in a range of about 1 D to about 4.5 D, wherein a depth-of-focus associated with at least one of the far or near focus is greater than about 1 D,
   wherein the optic further comprises an anterior and a posterior optical surface configured to provide the far focus, and a diffractive structure disposed on one of the surfaces providing the add power,
   wherein the add power of the IOL is selected as a function of a residual accommodation exhibited by the natural crystalline lens, such that a combination of the IOL and the natural crystalline lens provides a visual contrast greater than about 10% at a spatial frequency of about 20 cycles/degree for viewing objects at a distance greater than about 30 cm from the eye,
   wherein the visual contrast is characterized by a through-focus modulation transfer function (MTF) at a selected radiation wavelength and for a given aperture size, and,
   wherein the depth-of-focus associated with the far or near focus is selected such that a shift of the far or near focus of the eye caused by the residual accommodation of the natural crystalline lens results in an intermediate or a near vision, respectively, with a visual contrast greater than about 10% at a spatial frequency of about 20 cycles/degree.

2. The IOL of claim 1, wherein the depth-of-focus is in a range of about 1 D to about 4.5 D.

3. The IOL of claim 1, wherein the depth-of-focus is in a range of about 1 D to about 2.5 D for an add power in a range of about 1 to about 2.5 D.

4. The IOL of claim 1, wherein the depth-of-focus is in a range of about 2.5 D to about 4.5 D for an add power in a range of about 2.5 D to about 4.5 D.

5. The IOL of claim 1, wherein the optic provides a far-focusing power in a range of about −15 D to about +50 D Diopters.

* * * * *